(12) United States Patent
Peters et al.

(10) Patent No.: US 8,548,564 B2
(45) Date of Patent: Oct. 1, 2013

(54) TRACHEAL TUBE LOCATING SYSTEM AND METHOD

(75) Inventors: Daniel J. Peters, Longmont, CO (US); Edward McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 359 days.

(21) Appl. No.: 12/418,454

(22) Filed: Apr. 3, 2009

(65) Prior Publication Data
US 2010/0256482 A1   Oct. 7, 2010

(51) Int. Cl.
*A61B 5/00* (2006.01)

(52) U.S. Cl.
USPC .................. 600/424; 128/200.26; 128/207.14

(58) Field of Classification Search
USPC ................ 600/424; 128/200.26, 207.14, 899
See application file for complete search history.

(56) References Cited

U.S. PATENT DOCUMENTS

| | | | |
|---|---|---|---|
| 4,416,289 A | 11/1983 | Bresler | |
| 4,431,005 A | 2/1984 | McCormick | |
| 4,445,501 A | 5/1984 | Bresler | |
| 4,943,770 A | 7/1990 | Ashley-Rollman et al. | |
| 5,045,071 A * | 9/1991 | McCormick et al. | 604/529 |
| 5,139,019 A * | 8/1992 | Smith et al. | 128/207.15 |
| 5,425,382 A | 6/1995 | Golden et al. | |
| 5,560,351 A * | 10/1996 | Gravenstein et al. | 128/200.26 |
| 5,622,169 A | 4/1997 | Golden et al. | |
| 5,645,065 A | 7/1997 | Shapiro et al. | |
| 5,879,297 A | 3/1999 | Haynor et al. | |
| 5,902,238 A | 5/1999 | Golden et al. | |
| 6,129,668 A | 10/2000 | Haynor et al. | |
| 6,161,537 A | 12/2000 | Gravenstein et al. | |
| 6,216,028 B1 | 4/2001 | Haynor et al. | |
| 6,332,089 B1 | 12/2001 | Acker et al. | |
| 6,382,207 B1 * | 5/2002 | Giuffre et al. | 128/202.24 |
| 6,453,190 B1 | 9/2002 | Acker et al. | |
| 6,672,308 B1 | 1/2004 | Gaspari | |
| 7,265,551 B2 * | 9/2007 | Kellermann | 324/326 |
| 7,618,374 B2 * | 11/2009 | Barnes et al. | 600/466 |
| 8,073,229 B2 * | 12/2011 | Huo et al. | 382/132 |
| 2002/0066450 A1 | 6/2002 | Bonutti | |
| 2002/0074002 A1 | 6/2002 | Tung et al. | |
| 2008/0228066 A1 * | 9/2008 | Waitzman | 600/424 |
| 2009/0054760 A1 * | 2/2009 | Burke | 600/424 |

FOREIGN PATENT DOCUMENTS

WO   2009099766   8/2009

OTHER PUBLICATIONS

Gaspari et al., "Magnetically Guided Orotracheal Intubation," Mar. 2001, pp. 285-287, vol. 8, No. 3, Academic Emergency Medicine.

* cited by examiner

Primary Examiner — Ruth S Smith (57) ABSTRACT

According to various embodiments, a sensor may be placed on a patient chest adjacent to a desired position of a distal end of a tracheal tube. The sensor may be configured to emit an electromagnetic field into the patient and detect perturbations to that field caused by the presence of the tracheal tube. As the tube is inserted within the trachea, the sensor may detect the tube when the distal end passes within range of the sensor, indicating that a proper insertion depth has been reached. In certain embodiments, multiple sensors may be placed along the chest adjacent to the trachea to determine a distance between the tube and an anatomical structure. The distance information may provide an indication as to whether the tracheal tube is properly placed within the trachea.

20 Claims, 5 Drawing Sheets

TRACHEAL TUBE LOCATING SYSTEM AND METHOD

BACKGROUND OF THE INVENTION

The present disclosure relates generally to medical devices and, more particularly, to airway devices, such as tracheal tubes.

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea. Such tracheal tubes may include endotracheal (ET) tubes, tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, a patient may be intubated by insertion of an endotracheal tube through the patient's mouth and into the trachea. Often, such intubation procedures may be performed during medical emergencies or during critical care situations. As such, healthcare providers may balance a desire for speed of intubation with a desire for accurate placement of the tube within the trachea. However, proper placement of a tracheal tube may be complex. In certain situations, placement may be aided with visualization of the trachea performed during laryngoscopy. During an intubation procedure, a practitioner may employ a lighted laryngoscope during introduction of the endotracheal tube. However, often the visualization of the trachea is poor because of patient secretions that may obscure the laryngoscope. In addition, such visualization during introduction of the tube may not account for ongoing changes in the tube position within the trachea that may occur when a patient coughs, which may dislodge a tube from its desired location, or when a patient is jostled or moved within a care setting, which may change the position or angle of the tube within the trachea.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

Some embodiments described herein are directed to a method for determining placement of a tracheal tube in a subject. The method may include disposing an antenna or electrode outside of the subject and generally adjacent to the skin of the subject in a location corresponding to an anticipated location of the tracheal tube. The method may also include emanating an electromagnetic field from the antenna and detecting a perturbation to the electromagnetic field caused by the tracheal tube or a field-affecting feature on or in the tracheal tube. Furthermore, the method may include generating an output signal based upon the electromagnetic field perturbation.

Other embodiments described herein are directed to a system for determining placement of a tracheal tube in a subject. The system may include a field generating device configured to generate an electromagnetic field that emanates into the subject adjacent to the skin of the subject in a location corresponding to an anticipated location of the tracheal tube. The system may also include a field perturbation detecting device configured to detect a perturbation to the electromagnetic field caused by the tracheal tube or a field-affecting feature on or in the tracheal tube. Furthermore, the system may include a signal generating device configured to generate an output signal based upon the electromagnetic field perturbation.

Further embodiments described herein are directed to a system for determining placement of a tracheal tube in a subject. The system may include a tracheal tube configured to be disposed in a trachea of the subject. The system may also include at least one sensor positionable outside of the subject at a location corresponding to an anticipated location of the tracheal tube, and configured to emanate an electromagnetic field into the subject, detect perturbations to the electromagnetic field caused by a capacitance of the tracheal tube, and generate a signal based upon the perturbations. Furthermore, the system may include a monitor coupled to the at least one sensor and configured to provide an indication to a human user of a position of the tracheal tube in the subject based upon the signal.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A tracheal tube may be used to seal a patient airway and provide positive pressure to the lungs when properly inserted into a patient trachea. Positioning the tracheal tube at a desired position within the trachea, for example during endotracheal intubation, may improve the performance of the tracheal tube and reduce clinical complications. In particular, the distal inserted end of the endotracheal tube may be positioned in the patient trachea at a location substantially between the vocal cords and carina. If a tube cuff is not inserted far enough past the vocal cords, for example, the tube may become more easily dislodged. If the tube is inserted too far into the trachea, such as past the carina, then the tube may only function to adequately ventilate one of the lungs, rather than both. Thus, proper placement of the distal tip of the tube may result in improved ventilation to the patient.

Provided herein are tracheal tubes, systems and methods for facilitating proper placement of the tracheal tube relative to certain anatomical structures in and around the patient airway and trachea. In certain embodiments, a sensor may be placed on a patient chest adjacent to a desired position of a particular part or parts of the tracheal tube. The sensor may be configured to emit an electromagnetic field into the patient and to detect perturbations to that field caused by the presence of the tracheal tube. For example, a capacitance sensor may emit a field to detect changes in the dielectric constant of any tissue and objects falling within the effective range of the field, such as due to the presence of the tracheal tube. Similarly, an inductance sensor may emit a field to detect field variations due to the presence of the tracheal tube. As the tube is inserted within the trachea, the sensor may detect the tube when the distal end or any other particular part of the tube passes within range of the sensor, indicating that a proper insertion depth has been reached. Alternatively, if the position of the tracheal tube varies from the desired location, the sensor may detect the variation, indicating that adjustment of the tube may be in order. In certain embodiments, multiple sensors may be placed along the chest adjacent to the trachea to determine the position of the tube with respect to anatomical structures. A healthcare provider may then use the information about the location of the tracheal tube relative to the anatomical structures (e.g., the carina) to determine whether the tube is properly placed or whether the position of the tube should be adjusted.

In certain embodiments, the disclosed tracheal tubes, systems, and methods may be used in conjunction with any appropriate medical device, including without limitation a feeding tube, an endotracheal tube, a tracheotomy tube, a circuit, an airway accessory, a connector, an adapter, a filter, a humidifier, a nebulizer, nasal cannula, or a supraglottic mask/tube. The present techniques may also be used to monitor any patient benefiting from mechanical ventilation, e.g., positive pressure ventilation. Further, the devices and techniques provided herein may be used to monitor a human patient, such as a trauma victim, an intubated patient, a patient with a tracheotomy, an anesthetized patient, a cardiac arrest victim, a patient suffering from airway obstruction, or a patient suffering from respiratory failure.

Figure 1:
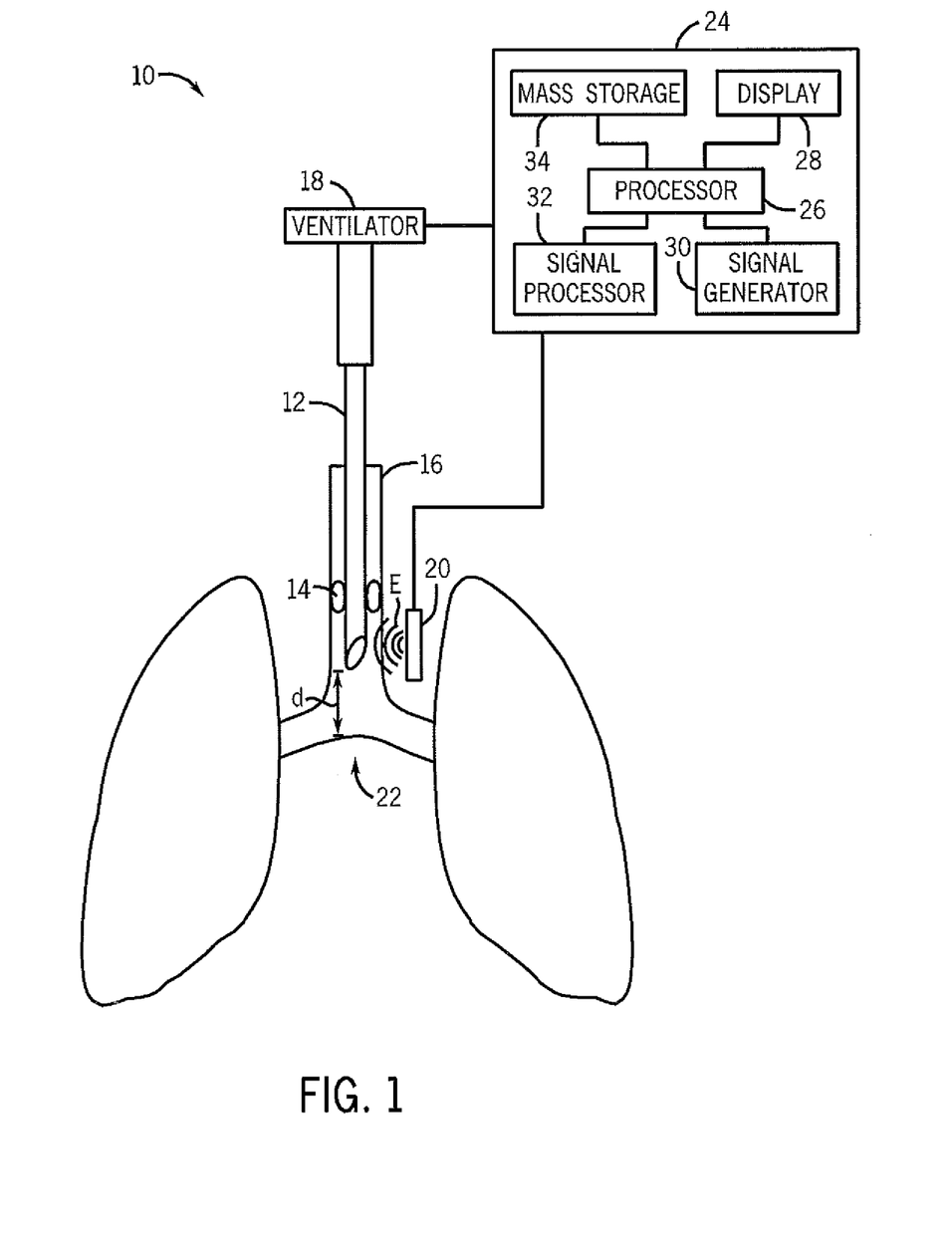
FIG. 1 is a schematic diagram of a system including a sensor configured to detect a position of a tracheal tube within a patient.

FIG. 1 is a schematic diagram of a tracheal tube system 10 that has been inserted into a patient trachea. The system 10 includes a tracheal tube 12, shown here as an endotracheal tube, with an inflatable balloon cuff 14 that may be inflated to form a seal against tracheal walls 16. When ventilation is provided via the tube system 10, a ventilator 18 is typically provided, as discussed below. As illustrated, the system 10 includes a sensor 20 (e.g., antenna) configured to emit an electromagnetic field E and detect perturbations to the field. The electromagnetic field may include an electric field, a magnetic field, or a combination thereof. Presence of the tracheal tube 12 within the trachea may interact with the electromagnetic field, thereby producing a perturbation detectable by the sensor 20. In general, the sensor 20 may detect a field perturbation within an effective range, typically fairly proximate to the sensor 20, depending upon such factors as the field strength, the amount and type of tissue through which the field emanates, the sensitivity of the sensor and associated electronic circuitry, and so forth. Therefore, as discussed in detail below, the sensor 20 may generate a signal indicative of the perturbation when the tube 12 is positioned adjacent to the sensor 20, that is, when the tube generally underlies the sensor location. For example, in certain embodiments, the sensor 20 may be coupled to the skin of the patient by a semi-permanent adhesive bond, or may simply be placed next to the skin or clothing of the patient via a hand-held probe or other packaging. As the tube 12 is inserted within the trachea, the sensor 20 may detect the presence of the tube 12 when the tube comes within range of the sensor 20. If the sensor 20 is positioned at a desired tube 12 location such as a distance d from an anatomical feature of interest (e.g., a carina 22), the tube 12 may be inserted along the trachea until the sensor 20 produces a signal indicative of tube presence. In this manner, the tracheal tube 12 may be properly positioned. As noted below, in certain cases, the tube itself may not sufficiently affect the field to produce the desired signal, and one or more features or devices may be placed in or on the tube to permit its detection. In such cases, such feature or features may be placed near the tube end or at any location or locations along the tube that provide a good indication of proper placement of the tube with respect to anatomical features of interest.

One such anatomical feature is typically the carina 22, which is a point along the cartilaginous ridge within the trachea between the two primary bronchi. Because the carina 22 is not visible to a physician or technician placing the sensor 20 on the patient, the sensor 20 may be positioned based on a location of an external feature (e g., the suprasternal notch). For example, the physician or technician may know or estimate the distance between the location of the suprasternal notch and the anatomical feature of interest (e.g., the carina 22), typically based upon the size of the patient. The physician or technician may then place the sensor 20 at a desired distance d from the carina 22 to detect when the tracheal tube 12 has reached the target location. In certain embodiments, multiple sensors 20 may be positioned along the length of the patient chest to determine tube 12 position. In such embodiments, tube 12 location may be ascertained by monitoring the sensor signals to identify which sensors 20 have detected the tube 12. Tube position may be approximately equal to the lowest (i.e., farthest down the trachea) sensor 20 that detects the presence of the tube 12.

When the system 10 includes devices that facilitate positive pressure ventilation of a patient, such as ventilator 18, any ventilator may be used, such as those available from Nelicor Puritan Bennett LLC. The system 10 also includes a monitor 24 that may be configured to implement embodiments of the present disclosure. The monitor 24 may be a stand-alone device or may be coupled to another patient monitor or to the ventilator 18. The monitor 24 may include a processor 26 and a display 28. The processor 26, or any other suitable processing circuitry, aids in determining tube presence and/or the distance d of the distal end of the tube 12 from reference structures within the patient, such as the carina 22.

The monitor 24 may include certain elements for controlling and/or receiving signals from the sensor 20. For example, in certain embodiments, the sensor 20 is configured to emit a field E into the patient and measure a change in capacitance indicative of tracheal tube 12 detection. Specifically, a permittivity (i.e., dielectric constant) of the tube 12 may be different from the permittivity of the surrounding tissues. Because capacitance is based on the permittivity of the dielectric (e.g., patient and tube 12), presence of the tube 12 may alter the net capacitance and be detected by the sensor 20 as a perturbation to the field E. In configurations employing capacitance sensors 20, a signal generator 30 within the monitor 24 may provide the sensor 20 with a direct current (DC) or alternating current (AC) electrical signal. Sensor 20 may convert this electrical signal into the field E that passes through the patient and tracheal tube 12. The sensor 20 may then generate an output signal representative of detected field. This signal may be received by the monitor 24 and analyzed by a signal processor 32. Depending upon the location of the sensor 20, or if more than one sensor 20 is utilized, the location of the lowest sensor 20 generating an output signal representative of detection, the signal processor 32 may convert the output signal into an electrical signal indicative of tube presence. The processed signal may then be conveyed to the processor 26 where the position d from the distal end of the tracheal tube 12 to the carina 22 is computed. In alternative embodiments, the sensor 20 may be configured to emit a field E into the patient and measure a change in inductance indicative of tracheal tube 12 detection. In such embodiments, the signal generator 32 and the signal processor 34 may function in a similar manner to the previously described embodiment with regard to generating and analyzing signals, respectively. In all cases, moreover, the sensor 20 may be temporarily positioned in the desired location (e.g., as a handheld probe), or may be semi-permanently secured to the patient, such as via adhesive or tape.

The monitor 24 may be configured to receive signals from the sensor 20 and store the signals in a storage device 34, such as RAM, PROM, optical read/write storage devices, flash memory devices, hardware storage devices, magnetic storage devices, or any other suitable device permitting memory storage. The signals may be accessed and operated upon according to instructions (which may also be stored in the memory circuitry) executed by the processor 26. In certain embodiments, the signals may be related to a placement of the tracheal tube 12 within the trachea and may be processed by the monitor 24 to indicate whether the tracheal tube 12 is properly placed. The monitor 24 may be configured to provide an indication about the placement of the tracheal tube 12 within the trachea, such as an audio alarm, visual alarm or a display message, as well as to provide special signals in the event the tracheal tube 12 is too far or too close to certain anatomical structures, such as the carina 22, or outside of a predetermined placement range, or whether the tube has moved or moved more than an allowed amount since its initial placement.

It should be noted, however, that while various processing may be performed based upon the detected perturbation to the emitted field, in some embodiments, the device may simply produce an indication that the tube is properly placed. For example, a feature on the tube may be placed at a location along the tube that, for the configuration of the tube and the size of the patient, may be detected by a properly placed field sensor when the tube is properly placed. For example, the detectable feature may be placed along the tube such that it may be detected in the vicinity of the suprasternal notch when the tube end is appropriately placed with respect to the patient carina. Upon detection of the feature, then, a visual or audible signal may be provided to the physician or technician.

Figure 2:
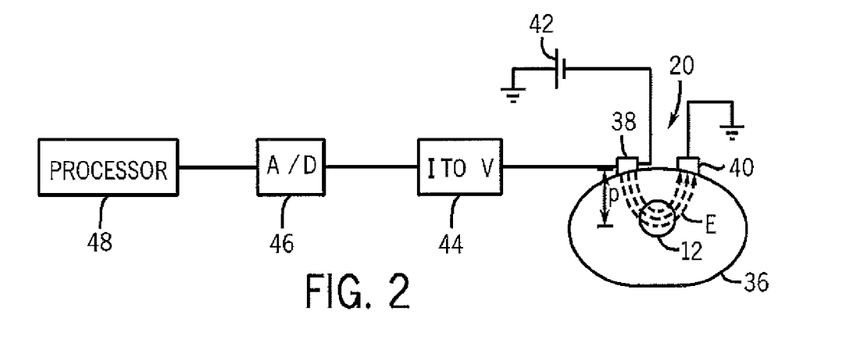
FIG. 2 is a detailed schematic diagram of a first embodiment of the sensor of FIG. 1 employing a direct current signal.

FIG. 2 is a detailed schematic diagram of a first embodiment of the sensor 20 of FIG. 1 employing a direct current signal. The sensor 20 of the present embodiment may be disposed on the chest of a patient 36 to detect the presence of the tracheal tube 12. Specifically, a pair of conductive parallel plates 38 and 40 may be positioned adjacent to the chest on opposite sides of the trachea. The plates 38 and 40 may be positioned such that the field E extends to a penetration depth p sufficient to detect the tube 12 The field E is generated by a potential difference between plate 38 and plate 40. As illustrated, a voltage is applied to plate 38 via a power supply 42, and plate 40 is grounded. While the power supply 42 and the plate 40 are connected to a ground, it should be appreciated that these grounds are not necessarily at zero voltage, but represent a common potential. Therefore, the voltage applied to plate 38 by the power supply 42 establishes a potential difference between the plates 38 and 40 of substantially the same magnitude as the power supply 42 output.

291 The field E may be measured by components including a current to voltage converter 44, an analog to digital converter (A/D) 46 and a processor 48. Specifically, plate 38 is connected to the current to voltage converter 44. Suitable converters 44 may include circuits having operational amplifiers, for example. As appreciated, current within plate 38 may be proportional to a magnitude of the field E or to a perturbation to the field. The converter 44 translates the current from plate 38 into a proportional voltage. Hence, the converter 44 produces an analog signal indicative of the magnitude of the field E or to a perturbation to the field. In alternative embodiments, the current to voltage converter 44 may be omitted and the analog signal may be generated by measuring voltage across plates 38 and 40.

The analog signal then enters the A/D converter 46, where the signal is converted into a digital signal. The processor 48 inputs the digital signal to compute a field-related signal that is indicative of detection of the tracheal tube. As previously discussed, field magnitude may vary based on the presence of the tracheal tube 12. For example, prior to tube insertion, the sensor 20 may be placed on the patient 36 to establish a baseline measurement of the field E. The processor 48 may store this baseline measurement and continuously (or from time to time) compare the magnitude of signals from the sensor to the stored value. If the processor 48 detects a change in the field-related signal greater than a programmed threshold value, for example, the processor 48 may indicate the presence of the tracheal tube 12 to the monitor 24.

Figure 3:
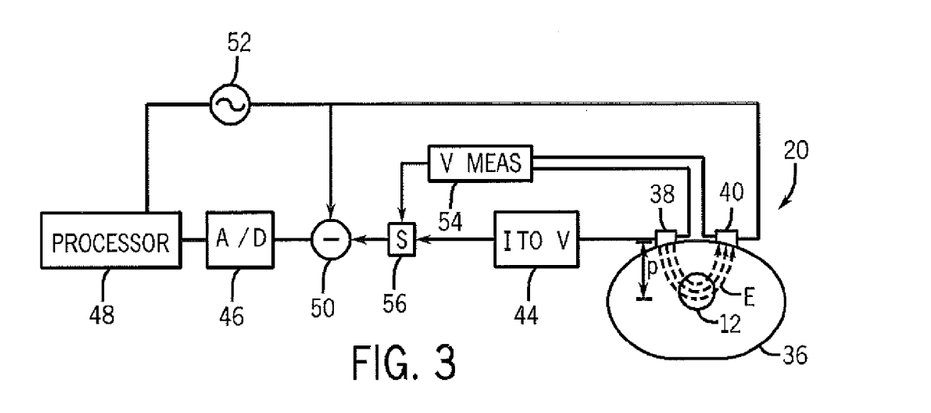
FIG. 3 is a detailed schematic diagram of a second embodiment of the sensor of FIG. 1 employing a constant-frequency alternating current signal.

FIG. 3 is a detailed schematic diagram of a second embodiment of the sensor 20 of FIG. 1 employing a constant-frequency AC signal. As illustrated, the present embodiment includes a junction 50, an oscillator 52, a voltage measurement unit (V MEAS) 54 and a switch 56. Specifically, the oscillator 52 is configured to apply a constant-frequency AC signal to plate 40. The frequency of oscillation may be selected based on desired penetration depth p. For example, frequencies below 1 GHz may penetrate the patient 36 to a depth p of approximately 8 cm. Such penetration depth p may be well-suited for tube 12 detection because it may generally be considered to include the trachea, although other depths may be utilized.

Similar to the embodiment employing a DC signal, interaction with the field E produces a change in the output signal from the sensor. Therefore, a current to voltage converter 44 is coupled to plate 38 to detect current variations and to output an analog signal indicative of current. In addition, a voltage measurement unit 54 is coupled to both plates 38 and 40. The unit 54 is configured to compare the voltage between plates 38 and 40 and output a signal indicative of the difference. Both the voltage measurement unit 54 and the current to voltage converter 44 are coupled to a switch 56. The switch 56 is configured to selectively send the voltage or current signal to the junction 50. The junction 50 compares the voltage or current signal to the original oscillator driving signal and outputs a signal indicative of the difference to the A/D converter 46. The A/D converter 46 coverts the analog signals to digital signals for processing by the processor 48. As appreciated, various properties of the voltage and/or current signal may be affected by the field perturbations. For example, in certain embodiments, the tracheal tube 12 may be detected based on a phase shift between the current and/or voltage signal and the original driving signal from the oscillator 52. The processor 48 may be configured to detect such a phase shift and indicate the presence of the tube 12 if the phase shift is greater than a predetermined threshold value, for example.

Figure 4:
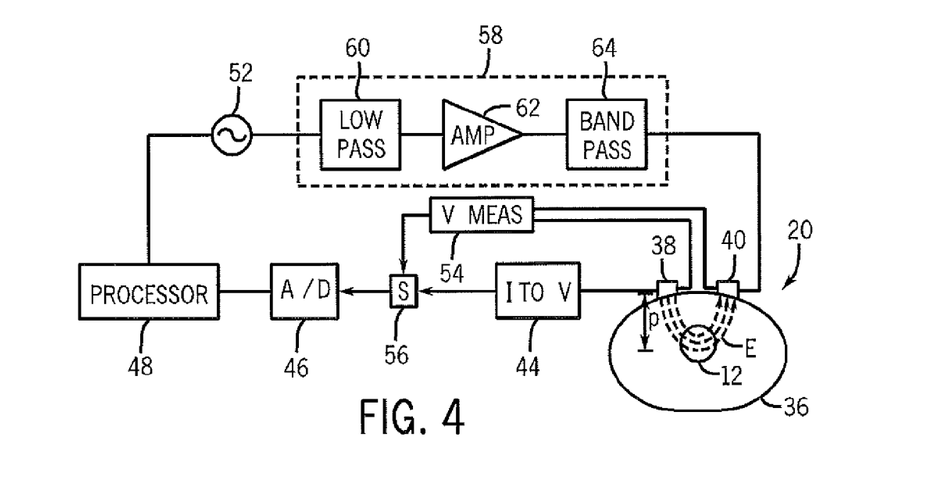
FIG. 4 is a detailed schematic diagram of a third embodiment of the sensor of FIG. 1 employing a variable-frequency alternating current signal.

FIG. 4 is a detailed schematic diagram of a third embodiment of the sensor 20 of FIG. 1 employing a variable-frequency AC signal. This embodiment is similar to the constant-frequency AC sensor 20 described above, except the driving frequency may vary with time. Specifically, the oscillator 52 is configured to emit a broad range of frequencies. For example, the oscillator 52 may be a voltage controlled oscillator (VCO) in which the frequency of oscillation is dependent on input voltage. The signal from the oscillator 52 may pass through a signal conditioning unit 58 configured to vary or "sweep" the frequency across the spectrum emitted by the oscillator 52. In practice, the device may utilize two or more discrete frequencies. The signal conditioning unit 58 includes a low pass filter 60, an amplifier 62, and a band pass filter 64. Parameters of each component within the signal conditioning unit 58 may be varied to sweep the driving frequency (or to selectively drive the sensor at two or more discrete frequencies). The output signal from the conditioning unit 58 is applied to plate 40, establishing a field E between plates 38 and 40.

Similar to the previously described embodiment, a current to voltage converter 44 is coupled to plate 38 to detect current variations and output an analog signal indicative of current. In addition, a voltage measurement unit 54 is coupled to both plates 38 and 40. The unit 54 is configured to compare the voltage between plates 38 and 40 and output a signal indicative of the difference. Both the voltage measurement unit 54 and the current to voltage converter 44 are coupled to the switch 56 which is configured to selectively send the voltage or current signal to the A/D converter 46. The A/D converter 46 coverts the analog signal to a digital signal for processing by the processor 48. The processor 48 may be configured to detect a phase shift and indicate the presence of the tube 12 if the phase shift is greater than a predetermined threshold value, for example.

As previously discussed, penetration depth p may be dependent upon the frequency of signals applied to the sensor. Therefore, sweeping across a frequency spectrum may serve to detect the tube 12 within any depth within the range of the fields generated by the frequencies utilized. In addition, certain materials may have a frequency dependent permittivity, causing the magnitude of field perturbations to vary with frequency. In certain embodiments, the processor 48 may be programmed with a characteristic permittivity of the tracheal tube 12, or the permittivity of any detection features formed in or on the tube. Therefore, sweeping across multiple frequencies while simultaneously searching for the permittivity signature of the tube 12 may enhance detection.

Figure 5:
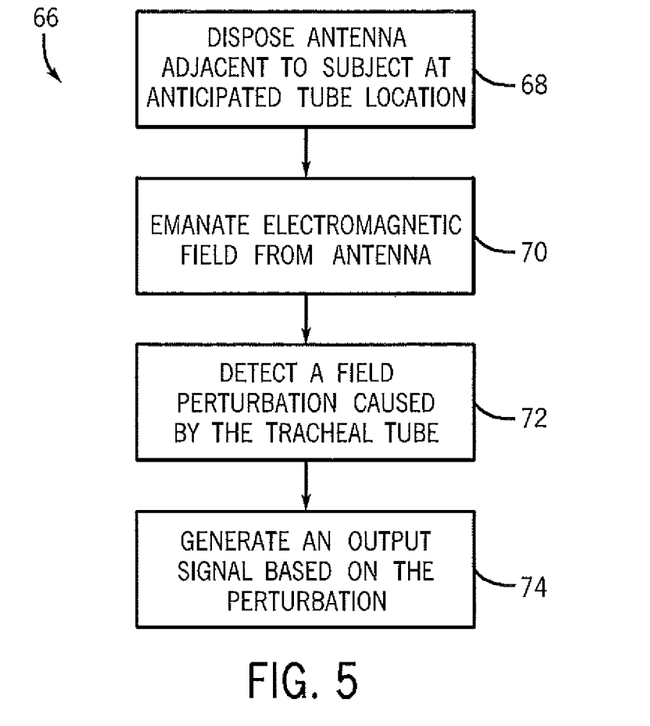
FIG. 5 is a flow diagram of a method for determining placement of the tracheal tube in the subject.

FIG. 5 is a process flow diagram illustrating an exemplary method in accordance with some embodiments. The method is generally indicated by reference number 66 and includes various steps or actions represented by blocks. First, as represented by block 68, the sensor or antenna 20 is disposed adjacent to the patient or subject 36 at an anticipated tube location. As previously discussed, this step may involve estimating the distance between an external structure and the anatomical feature of interest (e.g., carina 22), and placing the antenna 20 a desired distance from the feature. Next, a field E is emanated from the antenna 20, as represented by block 70. As represented by block 72, the antenna 20 detects a field perturbation caused by the tracheal tube 12. Finally, an output signal is generated based on the perturbation, as represented by block 74. This output signal may be utilized to determine the presence of the tracheal tube 12 within the trachea and/or the distance d between a distal end of the tube 12 and the carina 22. In certain embodiments, an audio and/or visual alarm may be activated when the tube is properly placed, or if the distance d deviates from a predetermined range, or if the sensor 20 fails to detect the tube 12 at a desired location. These steps may be performed during intubation or at any stage thereafter (e.g., after the cuff 14 has been inflated and the tube 12 is anticipated to remain relatively stationary).

Figure 6:
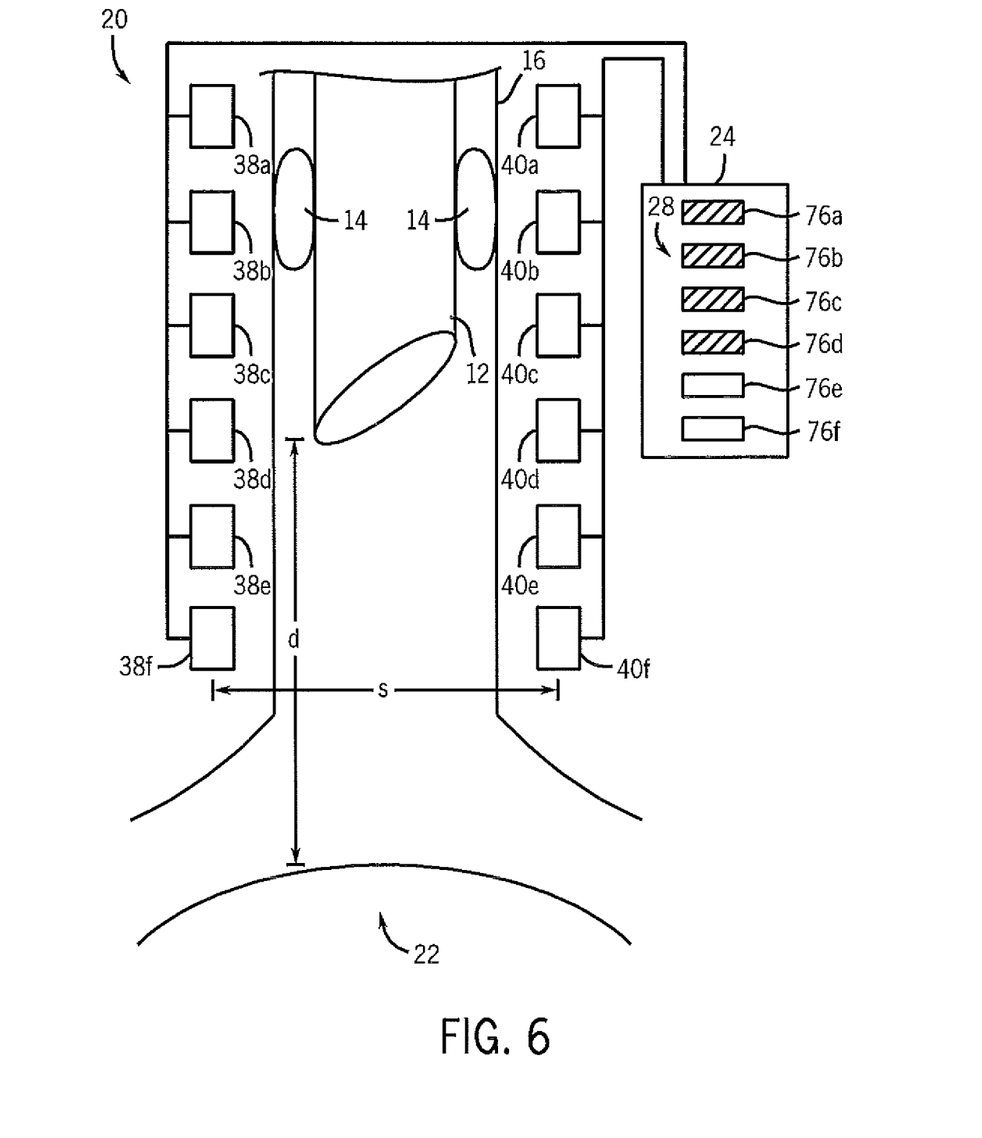
FIG. 6 is a cross-sectional side view of a distal end of the tracheal tube of FIG. 1 showing positions of sensors relative to the tracheal tube.

FIG. 6 is a cross-sectional side view of the distal end of the tracheal tube 12, showing positions of sensors 20 relative to the tracheal tube 12. This configuration may not only determine the presence of the tube 12 within the trachea, but also the distance d between the distal end of the tube 12 and the carina 22. An array of sensors 20 may be positioned on the chest of the patient 36, generally along the trachea. As previously described, each sensor 20 includes a pair of parallel plates 38 and 40. A field E may be established between the plates 38 and 40 to detect the presence of the tracheal tube 12. A spacing s between the plates 38 and 40 may be configured to provide sufficient penetration depth p to detect the tracheal tube 12.

As the tracheal tube 12 is inserted through the trachea, the field E between respective pairs of plates 38 and 40 may be perturbed. For example, as illustrated, the distal end of the tube 12 is positioned a distance d from the carina 22. Therefore, the tube 12 is proximate to the plate pairs 38a/40a, 38b/40b, 38c/40c, and 38d/40d. As a result, the tube 12 or a feature on or in the tube may interact with the field E between these sets of plates, causing perturbations that may be detected by the monitor 24 and conveyed to a human user via the display 28. The display 28 of the present embodiment includes a series of indicators 76, each corresponding to a pair of plates 38/40. As the tube 12 enters the detection range of each pair of plates 38/40, a respective indicator 76 may activate. In certain embodiments, these indicators 76 may include lights (e.g., LEDs) that illuminate based on tube detection. As illustrated, the indicators 76a, 76b, 76c and 76d are activated corresponding to tube detection between plates 38a/40a, 38b/40b, 38c/40c and 38d/40d. Indicators 76e and 76f are not activated, indicating that the tube 12 is not proximate to plates 38e/40e and 38f/40f. Therefore, the monitor 24 may convey to a human user that the distal end of the tube 12 is positioned between plates 38d and 40d. In certain embodiments, the color of the indicators 76 may vary based on desire tube 12 location. For example, the indicator 76 corresponding to sensors positioned at a desired tube location may be green. The indicators 76 directly above and below the desired tube location indicator 76 may be yellow, and the indicators 76 farther from the desired tube location indicator 76 may be red. The colors may be indicative of the offset between the distal end of the tube 12 and the desired distance d. In alternative embodiments, the display 28 may include a liquid crystal display (LCD) and the indicators 76 may be represented graphically on the LCD.

In certain embodiments, monitor 24 may be a hand-held device or probe that incorporates the sensors 20. For example, the sensors 20 may be mounted on a first side of the monitor 24 and the display 28 may be mounted on an opposite side. The sensor side of the monitor 24 may be placed against the skin of a patient chest. As the tracheal tube 12 is inserted into the trachea, the indicators 76 may activate in succession as the tube 12 approaches each sensor 20. The indicators 76 may be placed directly above respective sensors 20 such that the physician or technician may directly visualize the position of the tube 12 within the patient 36. For example, the bottom of the hand-held monitor 24 may be positioned directly above the carina 22. With the monitor 24 in this position, the physician or technician may insert the tube 12 to a desired distance d from the carina 22 by observing the indicators 76 on the display 28. For example, if the indicators 76 and the corresponding sensors 20 are positioned approximately 1 cm apart and the desired distance d is approximately 2 cm, the physician or technician may insert the tube 12 until the indicator 76d is activated. As previously discussed, the physician or technician may locate the carina 22 by estimating its distance from an external structure such as the suprasternal notch.

Proper tube placement may involve adjusting tube insertion depth to achieve a distance d between approximately 1 cm to 5 cm. In certain embodiments, the monitor 24 may automatically compute the distance d and display a value indicative of distance d on the display 28. For example, the display 28 may express the distance d in terms of inches or millimeters between the distal end of the tube 12 and the carina 22. In alternative embodiments, the display 28 may display a graphical representation of a trachea, including the carina 22 and the tracheal tube 12. In this manner, a clinician may utilize the image on the monitor 24 to determine proper tube placement.

Further embodiments may include an audible and/or visual alarm that is activated if the distance d varies from a predetermined range, or if the tube 12 is detected to move more than a desired amount from a known or initial position. It should be appreciated that there may be several empirically derived target ranges, depending on the size, age, or gender of the patient. A target range to which the distance d may be compared may differ for adult men, who may have, in an embodiment, a target range of about 3-4 cm, and adult women, for whom the target range may be about 2-3 cm. The alarm may indicate to a clinician that the distance d has deviated from the target range. In other embodiments, the alarm may be triggered if the distance d is less than 3 cm, less than 2 cm, or less than 1 cm.

Figure 7:
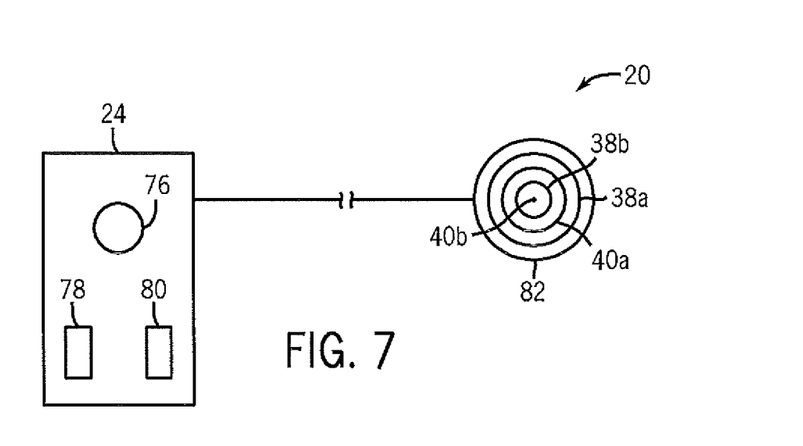
FIG. 7 is a schematic view of a hand-held monitor and an adhesively applied sensor.

FIG. 7 is a schematic view of an alternative embodiment of the system 10 including a hand-held monitor 24 and an adhesively applied sensor 20. While a single sensor 20 is connected to the hand-held monitor 24 in the present embodiment, it should be appreciated that multiple sensors 20 may be employed in further embodiments. The hand-held monitor 24 includes a single indicator 76 configured to activate if the sensor 20 detects the presence of tube 12 within the trachea. The hand-held monitor 24 also includes a power switch 78 and a calibration switch 80. The calibration switch 80 may be engaged to establish a baseline field E. For example, the sensor 20 may be placed on the patient chest adjacent to a desired location of the distal end of the tube 12. The calibration switch 80 may be engaged to measure and store the field-related signal without the tube 12 present. The tube 12 may then be inserted into the trachea until the indicator 76 is activated. Activation of the indicator 76 may inform a human user that the sensor 20 has detected a field perturbation indicative of the distal end of the tube 12 reaching a location proximate to the sensor 20. In this manner, the tube 12 may be properly positioned at a distance d from the carina 22, for example.

Alternatively, the tube 12 may be inserted within the trachea to a desired distance d from the carina 22. The sensor 20 may then be placed proximate to the distal end of the tube 12 and the calibration switch 80 may be engaged to measure and store a baseline field-related signal with the tube 12 present. If the tube 12 moves outside of sensor range, the indicator 76 and/or an audible alarm may activate, informing a human user that repositioning of the tube 12 is indicated. However, such a configuration may only inform the human user if the distance d increases such that the tube 12 is no longer proximate to the sensor 20. The indicator 76 may not activate if the distance d decreases because the tube 12 (although not the distal end) is still proximate to the sensor 20. Therefore, as described in detail below, the distal end of the tube 12 may include a field-affecting feature detectable by the sensor 20. In this configuration, if the field-affecting feature moves out of sensor range, the indicator 76 may activate even though a portion of the tube 12 is still proximate to the sensor 20.

While the previously described parallel plate sensors 20 may be used with the hand-held monitor 24. FIG. 7 illustrates an alternative sensor configuration. Specifically, the sensor 20 may be a medical electrode 82, having an adhesive side configured to attach to the skin of the patient 36. The adhesive side includes plates 38 and 40 arranged in concentric rings such that coupling the electrode 82 to the patient 36 establishes contact between the rings 38 and 40 and patient skin. The electrode 82 includes an outer set of rings 38a and 40a configured to emit a first field into the patient 36, and an inner set of rings 38b and 40b configured to emit a second field into the patient 36. The electrode 82 may be configured such that a perturbation to either field is detected by the monitor 24. The number of rings and the shape of each ring may vary in alternative embodiments. As appreciated, ring configuration may be adjusted to correspond to a particular frequency or frequencies of the electromagnetic field.

Figure 8:
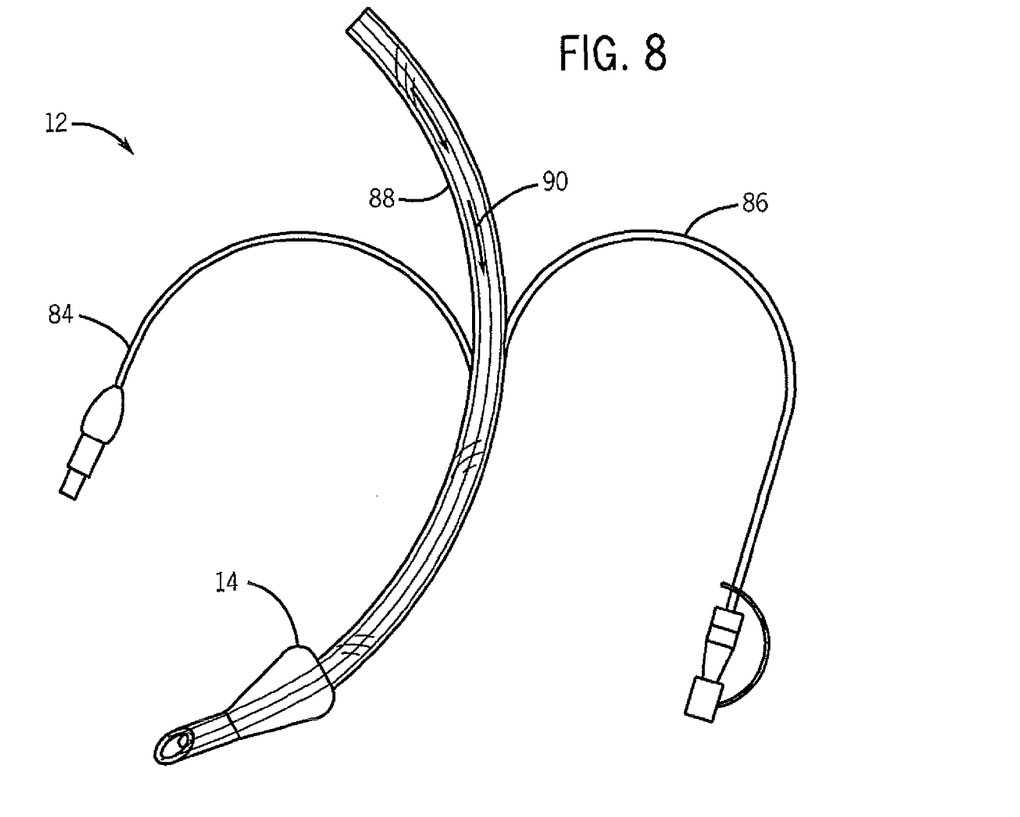
FIG. 8 is a perspective view of the tracheal tube of FIG. 1.

FIG. 8 is a perspective view of a tracheal tube 12 according to certain embodiments of the present techniques. As shown, the tube 12 includes a cuff 14 that may be inflated via inflation lumen 84. The tracheal tube 12 also includes a suction lumen 86 for aspirating secretions that may form above the cuff 14. The tube 12 and the cuff 14 may be formed from materials having suitable mechanical properties (such as puncture resistance, pin hole resistance, tensile strength), and chemical properties (such as biocompatibility). In one embodiment, the walls of the cuff 14 are made of a polyurethane having suitable mechanical and chemical properties. An example of a suitable polyurethane is Dow Pellethane® 2363-80A. In another embodiment, the walls of the cuff 14 are made of a suitable polyvinyl chloride (PVC). In one embodiment, the cuff 14 may be generally sized and shaped as a high volume, low pressure cuff that may be designed to be inflated to pressures between about 15 cm $H_2O$ and 30 cm $H_2O$. The system 10 may also include a respiratory circuit (not shown) connected to the endotracheal tube 12 that allows one-way flow of expired gases away from the patient and one-way flow of inspired gases toward the patient. The respiratory circuit, including the tube 12, may include standard medical tubing made from suitable materials such as polyurethane, polyvinyl chloride (PVC), polyethylene teraphthalate (ETP), low-density polyethylene (LDPE), polypropylene, silicone, neoprene, polytetrafluoroethylene (PTFE), or polyisoprene, In certain embodiments, the tube 12 may include a field-affecting feature configured to provide additional perturbation to the field, thereby enhancing tube detection by the sensor 20. For example, capacitance sensors 20 detect perturbations to the field caused by variations in permittivity (i.e., dielectric constant) within the patient 36. As appreciated, different materials have different dielectric constants. Therefore, the tube 12 may include a field-affecting feature that increases the permittivity difference between the tube 12 and the patient 36. For example, the tube 12 may include a coating 88 having a substantially higher dielectric constant than the patient 36. Alternatively, the tube 12 may be coated with metal to reduce its dielectric constant. Certain tubes 12 may include a silver layer 88 to limit the growth of microbes on the surface of the tube 12. The silver layer 88 may serve to enhance detection by providing a larger perturbation to the field E due to the increased permittivity difference.

Further embodiments may include a field-affecting feature disposed within the tube 12. For example, a material having a higher or lower dielectric constant may be embedded within a tube wall. In certain embodiments, a conductive element (e.g., metal wire) may be disposed within the tube 12 and extend along its length. In embodiments employing AC sensors 20, the conductive element may be tuned to substantially correspond to a frequency emitted by the sensors 20. Such a configuration may establish a resonance between the sensors 20 and the field-affecting feature, thereby enhancing tube detection.

Alternative embodiments may only include a field-affecting feature at the distal end of the tube 12. In such embodiments, the monitor 24 may be configured to only detect field perturbations caused by the field-affecting feature. Therefore, the monitor 24 may only indicate the presence of the tube 12 when the sensor 20 is proximate to the distal end of the tube 12. As a result, if a single sensor 20 is secured to the patient 36 after the tube 12 has been inserted, the monitor 24 may detect a change in field due to the distal end of the tube 12 moving out of sensor range. This configuration may detect both an increase and decrease in the distance d with a single sensor 20.

Further embodiments may employ a field-affecting feature having a dielectric constant that varies along the length of the tube 12. The field-affecting feature may include a single element having a continuously variable dielectric constant or a series of elements, each having a different dielectric constant. For example, the dielectric constant may increase along the flow path 90 of air through the tube 12. In this configuration, a single sensor 20 may be used to determine the position of the tube 12 within the trachea. For example, after the tube 12 is inserted at a desired depth, a single sensor 20 may be placed on the patient chest anywhere along the path of the tube 12. The monitor 24 may then detect tube movement by an increase or decrease in field perturbation. Similarly, the resonance frequency of the field-affecting feature may vary along the length of the tube 12. In this configuration, the sensor 20 may sweep across a frequency range to determine the maximum perturbation to the field. Because the maximum perturbation may occur at the resonance frequency, the monitor 24 may compare the resonance frequency to a stored value corresponding to a position along the tube 12 to determine tube insertion depth. As appreciated, similar configurations may be employed for inductive tube sensing For example, the tube 12 may include a coating and/or an internal element having an inductance that varies along the length of the tube 12. This configuration may enable the monitor 24 to compute tube position with a single inductive sensor 20.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of tracheal tube placement relative to anatomical structures in the trachea, but these techniques may also be utilized for the measurement and/or analysis of the placement of other suitable medical devices relative to other anatomical structures. For example, the present techniques may be utilized for the measurement and/or analysis of tracheal tubes relative to tracheal walls or the vocal cords. In addition, the present techniques may be employed in determining appropriate placement of any medical device, such as a stent, catheter, implant, feeding tube, cardiac device, drug delivery device, or pump. Rather, the various embodiments may cover all modifications, equivalents, and alternatives falling within the spirit and scope of the disclosure as defined by the following appended claims.

What is claimed is:

1. A method for determining placement of a tracheal tube in a subject comprising:
    disposing an antenna outside of the subject and generally adjacent to a skin of the subject in a location corresponding to an anticipated location of the tracheal tube;
    emanating an electromagnetic field from the antenna;
    detecting a perturbation to the electromagnetic field caused by one or more materials embedded in a wall of the tracheal tube, wherein the one or more materials comprise a material with a dielectric constant that varies along a length of the tracheal tube, and wherein the material with the dielectric constant that varies along the length of the tracheal tube causes the detected electromagnetic field perturbation to vary; and
    generating an output signal based upon the electromagnetic field perturbation, wherein the output signal provides an indication of a position of the tracheal tube in the subject.

2. The method of claim 1, wherein the perturbation to the electromagnetic field is detected via the antenna.

3. The method of claim 1, wherein the antenna is adhesively secured to the skin of the subject.

4. The method of claim 1, wherein emanating the electromagnetic field comprises sweeping a range of frequencies via the electromagnetic field.

5. The method of claim 1, wherein detecting the perturbation to the electromagnetic field comprises detecting a change in capacitance.

6. The method of claim 1, comprising determining a distance between a distal end of the tracheal tube and a physiological structure of the subject based at least in part upon the output signal.

7. A system for determining placement of a tracheal tube in a subject comprising:
    a tracheal tube configured to be disposed in a trachea of the subject;
    a field generating device configured to generate an electromagnetic field that emanates into the subject adjacent to a skin of the subject in a location corresponding to an anticipated location of the tracheal tube;
    a field perturbation detecting device configured to detect a perturbation to the electromagnetic field caused by one or more materials embedded in a wall of the tracheal tube, wherein the one or more materials comprise a material with a dielectric constant that varies along a length of the tracheal tube, and wherein the material with the dielectric constant that varies along the length of the tracheal tube causes the detected electromagnetic field perturbation to vary; and a signal generating device configured to generate an output signal based upon the electromagnetic field perturbation, wherein the output signal provides an indication of a position of the tracheal tube in the subject.

8. The system of claim 7, wherein the field generating device includes an antenna configured to be adhesively secured to the subject for at least emanating the electromagnetic field.

9. The system of claim 8, wherein the antenna is configured to detect the field perturbations.

10. The system of claim 8, comprising a second antenna configured to be adhesively secured to the subject for detecting the field perturbations.

11. The system of claim 7, wherein the field generating device, the field perturbation detecting device and the signal generating device are housed in a hand-held probe.

12. The system of claim 7, comprising a processor configured to determine a distance between a distal end of the tracheal tube and a physiological structure of the subject based at least in part upon the output signal.

13. A system for determining placement of a tracheal tube in a subject comprising:

a tracheal tube configured to be disposed in a trachea of the subject;

at least one sensor positionable outside of the subject at a location corresponding to an anticipated location of the tracheal tube, and configured to emanate an electromagnetic field into the subject, detect perturbations to the electromagnetic field caused by a capacitance of a material embedded in a wall of the tracheal tube, and generate a signal based upon the perturbations, wherein the material comprises a material with a dielectric constant that varies along a length of the tracheal tube, and wherein the material with the dielectric constant that varies along the length of the tracheal tube causes the electromagnetic field perturbations to vary; and a monitor coupled to the at least one sensor and configured to provide an indication to a human user of a position of the tracheal tube in the subject based upon the signal.

14. The system of claim 13, comprising a plurality of sensors configured to be disposed along a length of the subject in a general direction of the trachea.

15. The system of claim 14, comprising a plurality of indicators, wherein each indicator corresponds to a sensor from the plurality of sensors, and wherein the monitor is configured to activate each indicator in response to receiving the signal from a corresponding sensor.

16. The system of claim 15, wherein each indicator of the plurality of indicators is configured to emit a first color if the monitor determines that the tracheal tube is properly positioned at a corresponding sensor and a second color if the monitor determines that the tracheal tube is not properly positioned at a corresponding sensor.

17. The system of claim 14, wherein the monitor is configured to provide an indication of the position of the tracheal tube based upon relative signal strength from the plurality of sensors.

18. The system of claim 13, wherein the monitor is configured to emit an audible alarm if the position of the tracheal tube in the subject deviates from a predetermined range.

19. The system of claim 13, wherein the dielectric constant of the material increases along a flow path of air through the tracheal tube.

20. The system of claim 13, wherein the monitor is configured to determine a distance between a distal end of the tracheal tube and a physiological structure of the subject based at least in part upon the signal.

* * * * *